United States Patent
Kim et al.

(10) Patent No.: US 9,551,709 B2
(45) Date of Patent: Jan. 24, 2017

(54) UNIVERSAL NUCLEIC ACID APTAMERS FOR COMMONLY BINDING TO VARIOUS TYPES OF MICROORGANISMS AND METHOD OF PRODUCING THE SAME

(71) Applicant: KOREA INSTITUTE OF SCIENCE AND TECHNOLOGY, Seoul (KR)

(72) Inventors: Byoung Chan Kim, Seoul (KR); Min Young Song, Seoul (KR); Jin Yang Chung, Seoul (KR); Jong Soo Jurng, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/623,082

(22) Filed: Feb. 16, 2015

(65) Prior Publication Data

US 2015/0260717 A1 Sep. 17, 2015

(30) Foreign Application Priority Data

Mar. 12, 2014 (KR) ........................ 10-2014-0029274

(51) Int. Cl.
*C07H 21/02* (2006.01)
*G01N 33/569* (2006.01)
*C12N 15/10* (2006.01)
*G01N 33/53* (2006.01)

(52) U.S. Cl.
CPC ..... *G01N 33/56938* (2013.01); *C12N 15/1048* (2013.01); *G01N 33/5308* (2013.01); *G01N 33/56916* (2013.01); *G01N 2333/245* (2013.01); *G01N 2333/26* (2013.01); *G01N 2333/265* (2013.01); *G01N 2333/31* (2013.01); *G01N 2333/32* (2013.01)

(58) Field of Classification Search
None
See application file for complete search history.

(56) References Cited

U.S. PATENT DOCUMENTS 5,270,163 A 12/1993 Gold et al.

FOREIGN PATENT DOCUMENTS

KR 1020140020042 A 2/2014
WO WO 2009041776 * 4/2009

OTHER PUBLICATIONS

Chang et al (Scientific Reports | 3 : 1863, 7 pages, 2013).*
Seo et al. Development of Rapid Detection Methods for Foodborne Pathogens Using aptamer bioreporter, Jan. 2012, Project Development Report(Project No. PJ007195), Korea.
Kim et al., Isolation and Characterization of DNA aptamers against *Escherichia coli* using a bacterial cell-systematic evolution of ligands by exponential enrichment approach, analytical Biochemistry 436 (2013) 22-28, Elsevier, 2013.

* cited by examiner

*Primary Examiner* — Richard Schnizer
(74) *Attorney, Agent, or Firm* — Goldilocks Zone IP Law

(57) ABSTRACT

Provided are a single-stranded nucleic acid aptamer simultaneously and specifically binding to various types of microorganisms, and a method of manufacturing the nucleic acid aptamer. For example, provided are a probe that is capable of simultaneously detecting or diagnosing a variety of microorganisms, and a method of manufacturing an aptamer having characteristics of such a probe.

9 Claims, 10 Drawing Sheets

SEQUENCE LISTING

<160> NUMBER OF SEQ ID NOS: 24

<210> SEQ ID NO 1
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 1
gggcgggggt gctgggggaa tggagtgctg cgtgctgcgg        40

<210> SEQ ID NO 2
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 2
catatccgcg tcgctgcgct cagacccacc actacgcacc        40

<210> SEQ ID NO 3
<211> LENGTH: 38
<212> TYPE: DNA
<213> ORGANISM: Artificial Sequence
<220> FEATURE:
<223> OTHER INFORMATION: Sequence of random region for aptamer

<400> SEQUENCE: 3

-continued

```
catatccgcg tcgctgcgct cagacccacc acccgccc                              38

<210> SEQ ID NO 4
<211> LENGTH: 30
<212> TYPE: DNA
<213> ORGANISM: Artificial Sequence
<220> FEATURE:
<223> OTHER INFORMATION: Sequence of random region for aptamer

<400> SEQUENCE: 4
cgaacgttgc ggtgtggaac ttcgcgagca                                       30

<210> SEQ ID NO 5
<211> LENGTH: 30
<212> TYPE: DNA
<213> ORGANISM: Artificial Sequence
<220> FEATURE:
<223> OTHER INFORMATION: Sequence of random region for aptamer

<400> SEQUENCE: 5
tgcggactcg cgatgctact tctgatgata                                       30

<210> SEQ ID NO 6
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 6
catatccgcg tcgctgcgct cagacccacc accacgcacc                            40

<210> SEQ ID NO 7
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 7
cgaccgcagg tgcaccgggc gacgtctctg ggtgtggtga                            40

<210> SEQ ID NO 8
<211> LENGTH: 30
<212> TYPE: DNA
<213> ORGANISM: Artificial Sequence
<220> FEATURE:
<223> OTHER INFORMATION: Sequence of random region for aptamer

<400> SEQUENCE: 8
tgcggactca tgatgctact tctgatgata                                       30

<210> SEQ ID NO 9
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 9 gggcggggggg tgctggggga atggagtgct gcgtgctgcg                           40

<210> SEQ ID NO 10
<211> LENGTH: 40
<212> TYPE: DNA
```

```
<213> ORGANISM: Artificial Sequence
<220> FEATURE:
<223> OTHER INFORMATION: Sequence of random region for aptamer

<400> SEQUENCE: 10 gggcggggt gctgggagaa tggagtgctg cgtgctgcag                              40

<210> SEQ ID NO 11
<211> LENGTH: 39
<212> TYPE: DNA
<213> ORGANISM: Artificial Sequence
<220> FEATURE:
<223> OTHER INFORMATION: Sequence of random region for aptamer

<400> SEQUENCE: 11
atatccgcgt cgctgcgctc agacccacca ccacgcacc                              39

<210> SEQ ID NO 12
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 12
catatccgtg tcgctgcgct cagacccacc accacgcacc                             40

<210> SEQ ID NO 13
<211> LENGTH: 30
<212> TYPE: DNA
<213> ORGANISM: Artificial Sequence
<220> FEATURE:
<223> OTHER INFORMATION: Sequence of random region for aptamer

<400> SEQUENCE: 13
ggactggagt ctagaccggg tagctgtggt                                        30

<210> SEQ ID NO 14
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 14
cgacgcgcgt tggtggtgga tggtgtgtta cacgtgttgt                             40

<210> SEQ ID NO 15
<211> LENGTH: 29
<212> TYPE: DNA
<213> ORGANISM: Artificial Sequence
<220> FEATURE:
<223> OTHER INFORMATION: Sequence of random region for aptamer

<400> SEQUENCE: 15
cggggtggga ccagtcttgc gcgggtgac                                         29

<210> SEQ ID NO 16
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 16
cgaccgcagg tgcactgggc gacgtctctg ggtgtggtgt                             40
```

<210> SEQ ID NO 17
<211> LENGTH: 30
<212> TYPE: DNA
<213> ORGANISM: Artificial Sequence
<220> FEATURE:
<223> OTHER INFORMATION: Sequence of random region for aptamer

<400> SEQUENCE: 17
cgaacggtgc ggtgtggaac ttcgcgagca                                      30

<210> SEQ ID NO 18
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 18
gggcaggtgt gctgggggaa tggagtgctg cgtgctgcgg                            40

<210> SEQ ID NO 19
<211> LENGTH: 40
<212> TYPE: DNA
<213> ORGANISM: Artificial Sequence
<220> FEATURE:
<223> OTHER INFORMATION: Sequence of random region for aptamer

<400> SEQUENCE: 19
ggaccgcagg tgcactgggc gacgtctctg ggtgtggtgt                            40

<210> SEQ ID NO 20
<211> LENGTH: 30
<212> TYPE: DNA
<213> ORGANISM: Artificial Sequence
<220> FEATURE:
<223> OTHER INFORMATION: Sequence of random region for aptamer

<400> SEQUENCE: 20
cgaacgttgc ggtgtggacc ttcgcgagca                                      30

<210> SEQ ID NO 21
<211> LENGTH: 40
<212> TYPE: DNA
<213> ORGANISM: Artificial Sequence
<220> FEATURE:
<223> OTHER INFORMATION: Sequence of random region for aptamer
<220> FEATURE:
<221> NAME/KEY: misc_feature
<222> LOCATION: (19)..(19)
<223> OTHER INFORMATION: n is a, c, g, or t

<400> SEQUENCE: 21
cgaccgcagg tgcactggnc gacgtctctg ggtgtggtgt                            40

<210> SEQ ID NO 22
<211> LENGTH: 76
<212> TYPE: DNA
<213> ORGANISM: Artificial Sequence
<220> FEATURE:
<223> OTHER INFORMATION: DNA pool for preparation of aptamer
<220> FEATURE:
<221> NAME/KEY: misc_feature
<222> LOCATION: (19)..(58)
<223> OTHER INFORMATION: n is a, c, g, or t

<400> SEQUENCE: 22

```
cgtacggaat tcgctagcnn nnnnnnnnnn nnnnnnnnnn nnnnnnnnnn nnnnnnnngg        60
atccgagctc cacgtg                                                         76

<210> SEQ ID NO 23
<211> LENGTH: 18
<212> TYPE: DNA
<213> ORGANISM: Artificial Sequence
<220> FEATURE:
<223> OTHER INFORMATION: primer for PCR

<400> SEQUENCE: 23
cgtacggaat tcgctagc                                                       18

<210> SEQ ID NO 24
<211> LENGTH: 18
<212> TYPE: DNA
<213> ORGANISM: Artificial Sequence
<220> FEATURE:
<223> OTHER INFORMATION: primer for PCR

<400> SEQUENCE: 24
cacgtggagc tcggatcc                                                       18
```

UNIVERSAL NUCLEIC ACID APTAMERS FOR COMMONLY BINDING TO VARIOUS TYPES OF MICROORGANISMS AND METHOD OF PRODUCING THE SAME

RELATED APPLICATION

This application claims the benefit of Korean Patent Application No. 10-2014-0029274, filed on Mar. 12, 2014, in the Korean Intellectual Property Office, the disclosure of which is incorporated herein in its entirety by reference.

BACKGROUND

1. Field

One or more embodiments of the present invention relate to a nucleic acid aptamer commonly and selectively binding to various types of microorganisms, and a method of manufacturing the same.

2. Description of the Related Art

An aptamer is generally referred to a single-stranded DNA or RNA having high specificity and affinity for a specific target material. Aptamers have advantages over antibodies in that aptamers have higher affinity for a target material than that of antibodies that are mainly used in the field of sensors for disease diagnostic technology, biosensor, or detection for harmful microorganism, and long-term storage of aptamers at room temperature is possible due to excellent thermal stability thereof. In addition, easy chemical synthesis of aptamers enables low cost and large scale production of aptamers with high purity without need to obtain antibodies by injecting antigens into animals. Therefore, many studies have been made on the development of aptamers having high specificity and affinity for a specific target material to take advantages in diagnostic and therapeutic techniques or in use of biosensors.

Systematic evolution of ligands by exponential enrichment (SELEX) techniques regarding aptamer selection are protected by essential patent of Gold and Tuerk disclosing "Methods for identifying nucleic acid ligands (refer to U.S. Pat. No. 5,270,163)", but the patent expired on Dec. 14, 2010. Accordingly, techniques regarding aptamer screen that are relatively less active until now become more active, and accordingly, a variety of modified SELEX methods are developed. For example, Cell SELEX refers to a method of selecting aptamers that have the highest binding force to a surface of whole cells, unlike conventional SELEX techniques that are used with respect to purified proteins or chemicals. Cell SELEX may be used in the case of attempting to recognize specific disease cells but failing to identify proteins associated with disease cells. Many studies on Cell SELEX have been made in terms of mainly recognizing and binding to a surface of specific cancer cells, and recently, studies on Whole Cell SELEX are reported with respect to microorganisms such as *Staphylococcus aureus* and *Escherichia coli*, respectively.

However, regarding the aptamer selection method using existing Cell SELEX, aptamers having high selectivity for only one kind of a target material are selected. In detail, the aptamer selection method includes (1) screening only nucleic acids capable of binding to one target material after mixing the target material, such as a specific target microorganism or protein, with a nucleic acid library consisting of random sequences; (2) removing nucleic acid structures that are not bound to the target material and obtaining the nucleic acids capable of binding to the target material; and (3) amplifying the nucleic acids for the next round's selection procedure. These steps (1) to (3) are repeated several to tens of times, thereby discovering nucleic acid aptamers having significantly high affinity and specificity for target materials. That is, the existing Cell SELEX has to limit the subject to one type of a target material without any other choices. However, types of microorganisms vary in rivers, foods, and environmental facilities, and in this regard, no invention has been reported yet relating to development of a universal DNA aptamer for recognizing, detecting, or diagnosing these various types of microorganisms and a method of manufacturing the universal DNA aptamer.

SUMMARY

One or more embodiments of the present invention include a nucleic acid aptamer capable of simultaneously and specifically detecting various types of microorganisms.

One or more embodiments of the present invention include a composition and a biosensor including the nucleic acid aptamer.

One or more embodiments of the present invention include a method of manufacturing the nucleic acid aptamer.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
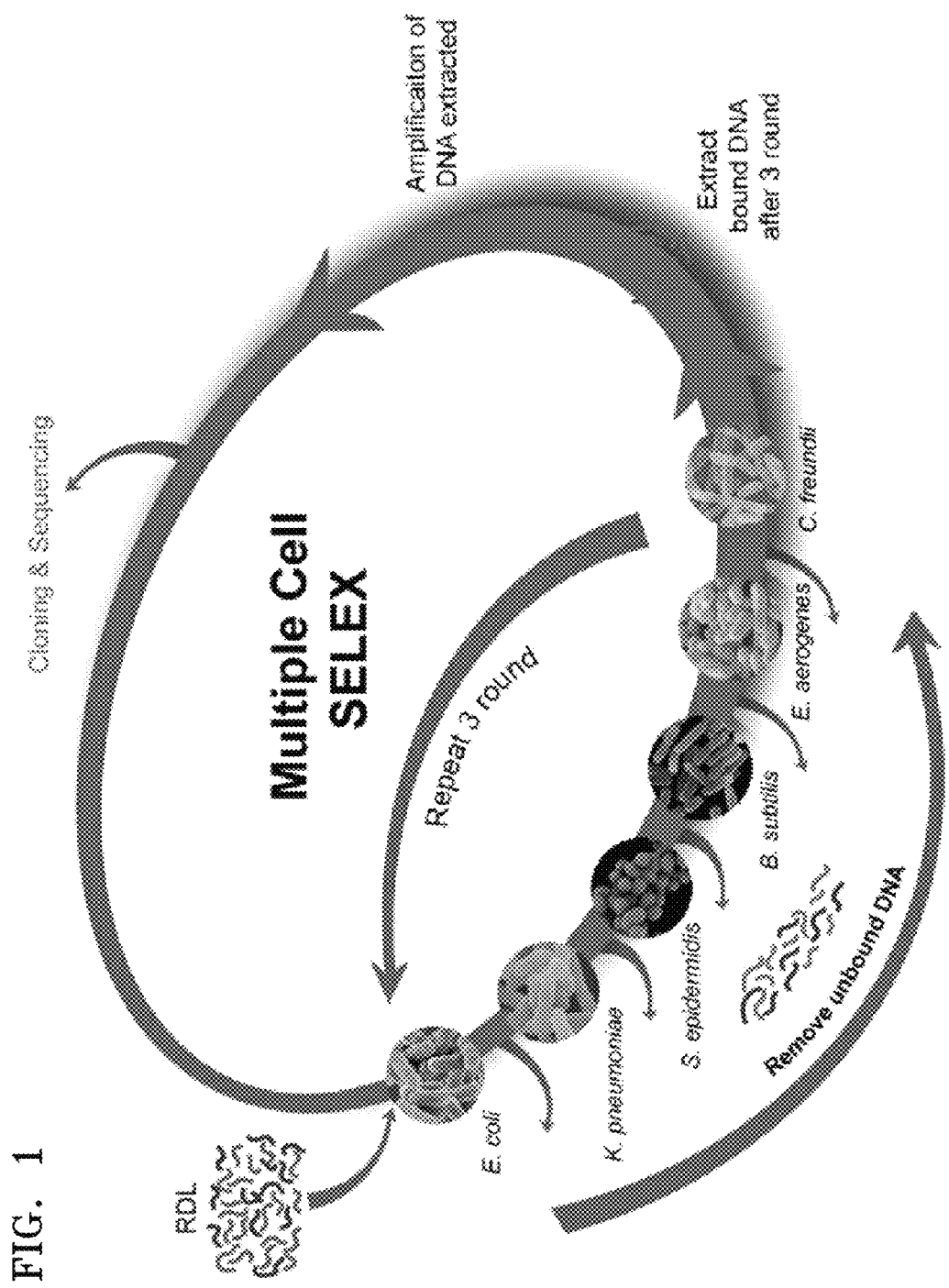
FIG. 1 is a schematic diagram illustrating a method of manufacturing a DNA aptamer that is capable of selectively binding to 6 types of microorganisms, according to an embodiment of the present invention.
Figure 2A:
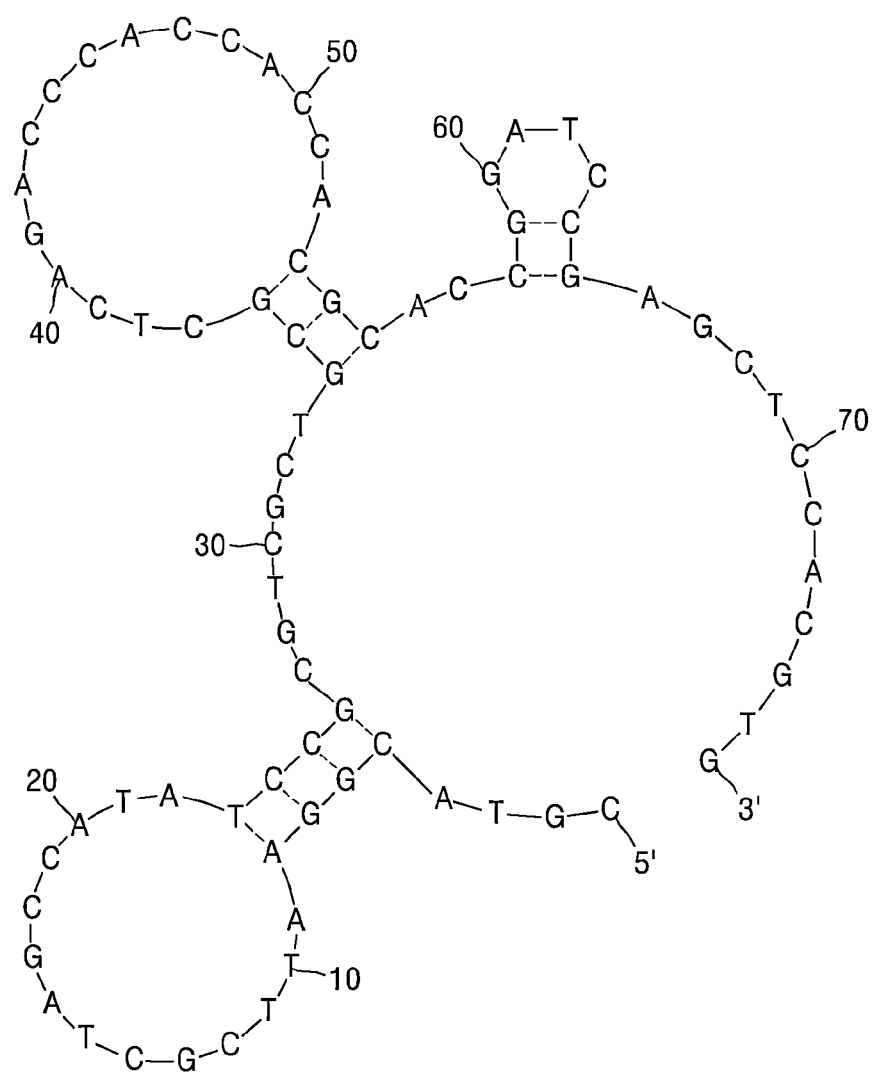
FIGS. 2A and 2B are schematic diagrams obtained by using mfold program showing secondary structures of two types of nucleic acid aptamers that are expected to have strong specificity and binding capability for 6 types of microorganisms, according to an embodiment of the present invention, and FIG. 2A refers to DNA aptamer No. 06 and FIG. 2B refers to DNA aptamer No. 19 DNA aptamer 6 comprises SEQ ID NO: 22 wherein the segment of 'n' residues at positions 19-58 was replaced by SEQ ID NO: 6. DNA aptamer 19 comprises SEQ ID NO: 22 wherein the segment of 'n' residues at positions 19-58 was replaced by SEQ ID NO: 19.
Figure 2B:
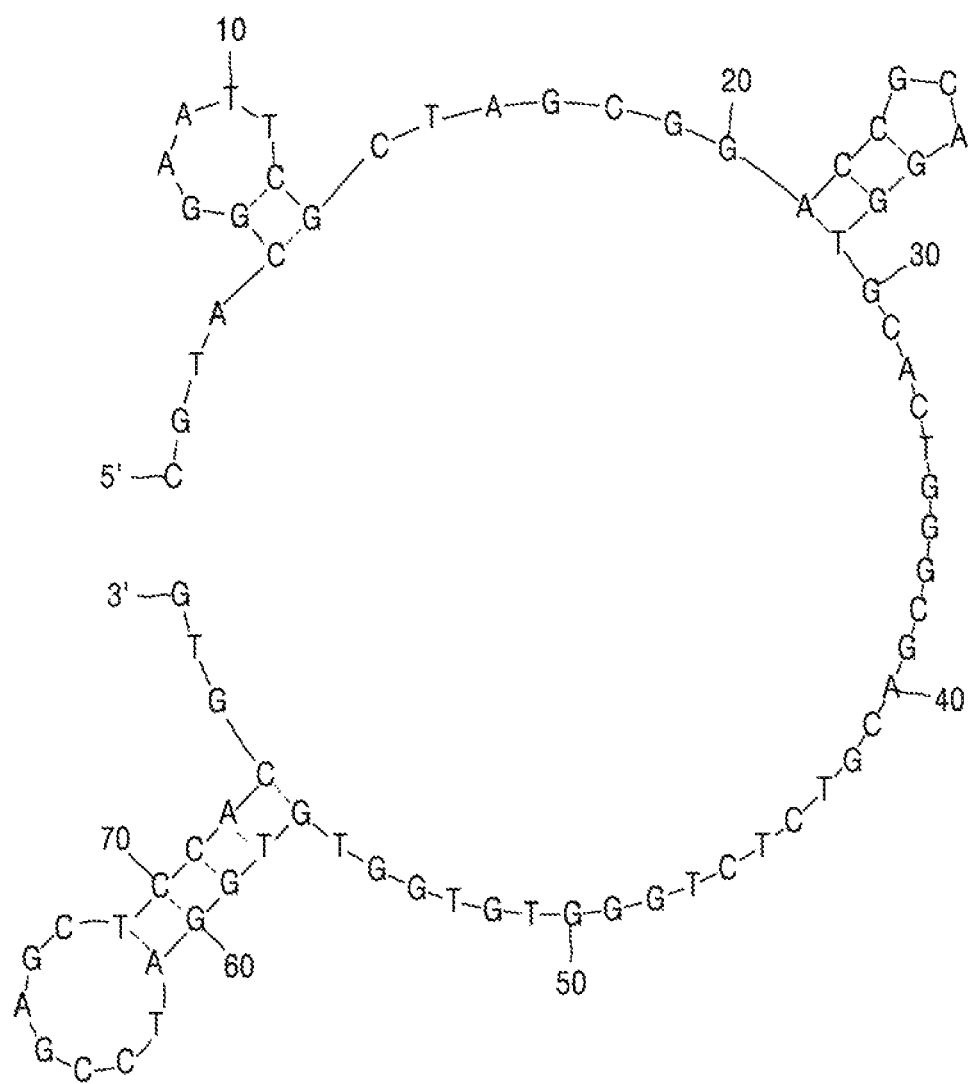
Figure 3A:
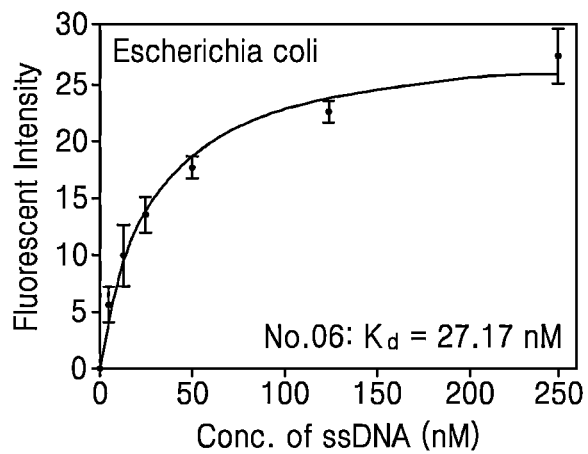
FIGS. 3A and 3B show the results of analyzing binding capability of DNA aptamer No. 06 and DNA aptamer No. 19 with respect to *Escherichia coli*, respectively.
Figure 3B:
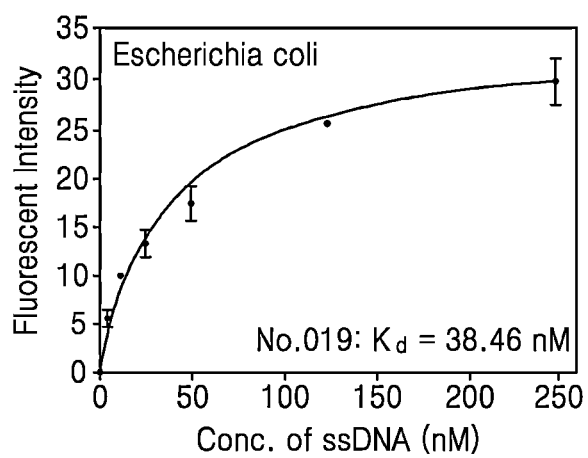
Figure 4A:
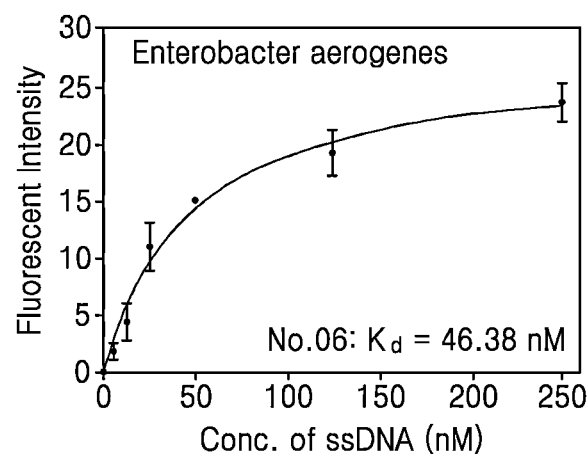
FIGS. 4A and 4B show the results of analyzing binding capabilitoy of DNA aptamer No. 06 and DNA aptamer No. 19 with respect to *Enterobacter aerogenes*, respectively.
Figure 4B:
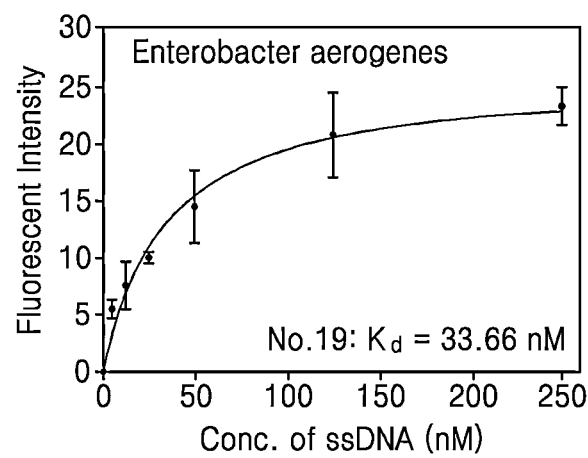
Figure 5A:
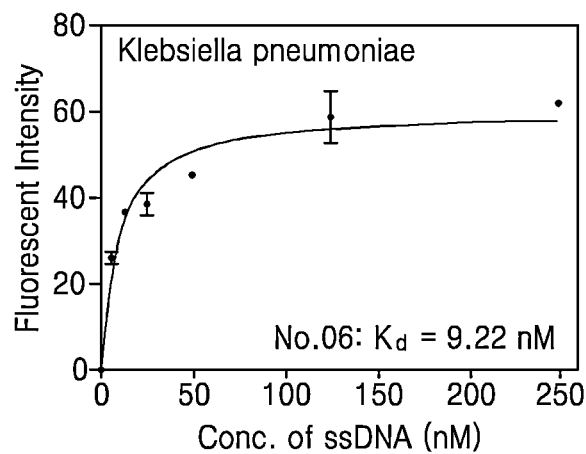
FIGS. 5A and 5B show the results of analyzing binding capabilitoy of DNA aptamer No. 06 and DNA aptamer No. 19 with respect to *Klebsiella pneumoniae*, respectively.
Figure 5B:
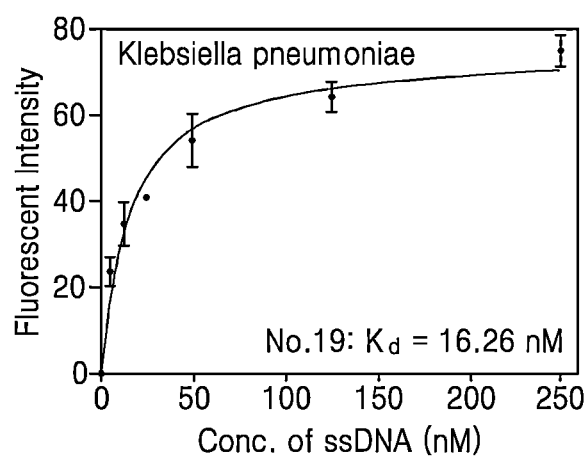
Figure 6A:
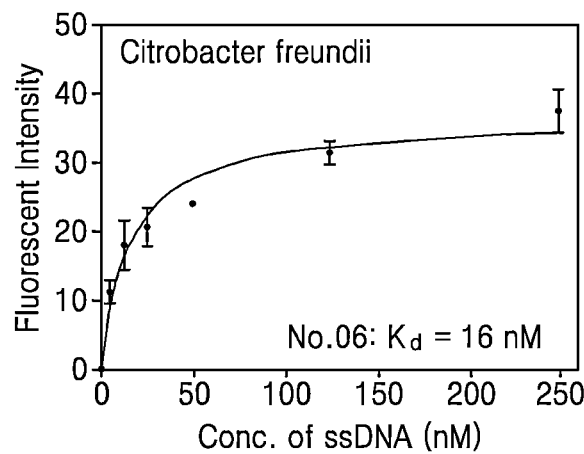
FIGS. 6A and 6B show the results of analyzing binding capabilitoy of DNA aptamer No. 06 and DNA aptamer No. 19 with respect to *Citrobacter freundii*, respectively.
Figure 6B:
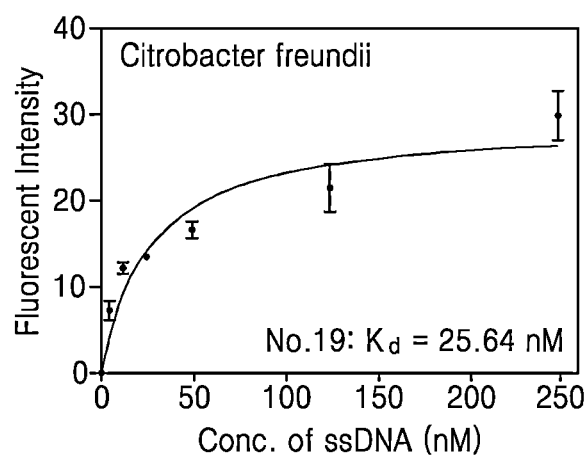
Figure 7A:
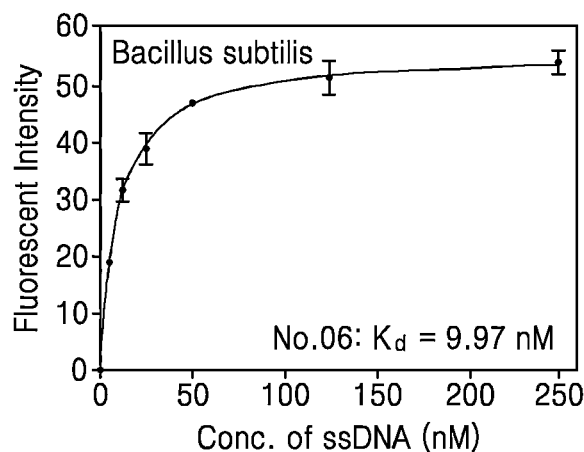
FIGS. 7A and 7B show the results of analyzing binding capabilitoy of DNA aptamer No. 06 and DNA aptamer No. 19 with respect to *Bacillus subtilis*, respectively.
Figure 7B:
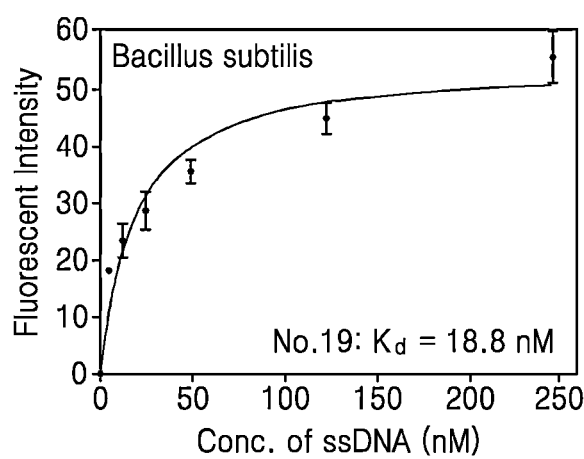
Figure 8A:
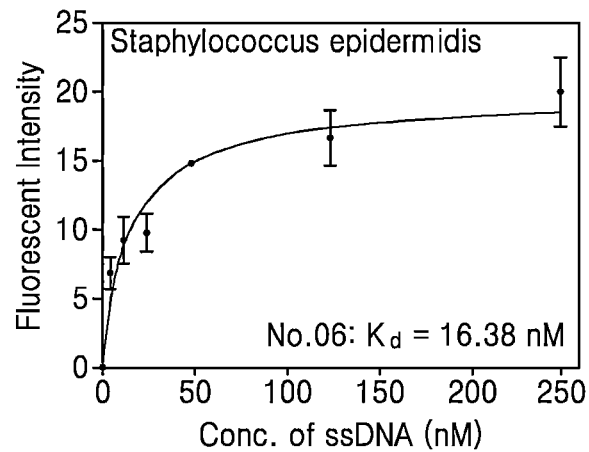
FIGS. 8A and 8B show the results of analyzing binding capabilitoy of DNA aptamer No. 06 and DNA aptamer No. 19 with respect to *Staphylococcus epidermidis*, respectively.
Figure 8B:
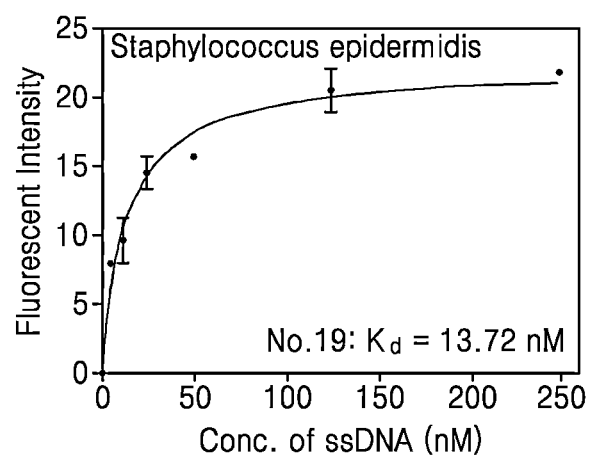

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, provided is a nucleic acid aptamer that commonly and selectively binds to two or more microorganisms.

The term "aptamer" as used herein refers to a molecule having a stable tertiary structure by itself and capable of binding to a target molecule with high affinity and specificity. The term "nucleic acid" as used herein refers to a polymer of nucleotides, and may be used in the same meaning as "oligonucleotide" or "polynucleotide". The nucleic acid may include DNA, RNA, and/or peptide nucleic acid (PNA). A nucleotide is a basic constitutional unit of a nucleic acid molecule which includes a deoxyribonucleotide or a ribonucleotide, and may include an analogue where a sugar or a base is modified in addition to a natural nucleotide. The aptamer may include a single-stranded nucleic acid, and the term "single-stranded nucleic acid" as used herein refers to a type of nucleic acid where the polymer of nucleotides is single-stranded.

The term "two or more microorganisms" as used herein refers to two or more types of microorganisms. The two or more types of microorganisms may refer to, for example, microorganisms each belonging to a different 'genus', or microorganisms each belonging to the same 'genus' but a different 'species'.

The term "commonly binding to microorganisms" as used herein refers that the aptamer of the present invention is able to bind to each of all the target microorganisms. That is, the aptamer of the present invention may target two or more microorganisms, unlike an aptamer of the related art which targets only one type of microorganisms in a limited way. The term "selectively binding to microorganisms" as used herein refers that the aptamer of the present invention is able to bind to a target microorganism but substantially fails to bind to a microorganism other than the target microorganism. Here, a term 'specifically binding to' may be used in place of the term 'selectively binding to'. The aptamer of the present invention is able to simultaneously recognize two or more microorganisms, and is also capable of specifically binding to two or more microorganisms. Therefore, the aptamer of the present invention is applicable to simultaneously detect two or more microorganisms that are present in a particular environment.

The aptamer may specifically bind to a surface of microorganisms. The term "specifically bind to a surface of microorganisms" as used herein refers that the aptamer may specifically binding to a protein present on a cell surface of each of the microorganisms, or a specific structure on the microbial surface. In this regard, the aptamer of the present invention is capable of directly binding to the cell surface of microorganisms without conducting a cell disruption process, and accordingly, may enable fast and accurate detection for the presence and concentration of target microorganisms.

The aptamer of the present invention may commonly and selectively bind to, for example, 2 or more, 3 or more, 4 or more, 5 or more, 6 or more, 7 or more, 8 or more, 9 or more, or 10 or more microorganisms. In addition, the aptamer of the present invention may simultaneously and selectively bind to, for example, 2 to 20, 3 to 18, 4 to 16, 5 to 14, 6 to 12, 6 to 10, 6 to 9, or 6 to 8 microorganisms. In addition, the aptamer of the present invention may simultaneously and selectively bind to, for example, 2, 3, 4, 5, or 6 microorganisms.

The target microorganisms of the aptamer may be selected from the group consisting of microorganisms belonging to genera *Escherichia, Enterobacter, Klebsiella, Citrobacter, Bacillus*, and *Staphylococcus*. For example, when the aptamer targets 2 or more microorganisms, at least one of the target microorganisms may be selected from the above-described group. In addition, for example, when the aptamer targets 6 microorganisms, at least one of the target microorganisms may be selected from the above-described group, or all the 6 target microorganisms may be selected from the above-described group.

The microorganism belonging to genus *Escherichia* may be, for example, *E. coli*. The microorganism belonging to genus *Enterobacter* may be, for example, *E. aerogenes*. The microorganism belonging to genus *Klebsiella* may be, for example, *K. pneumoniae*. The microorganism belonging to genus *Citrobacter* may be, for example, *C. freundii*. The microorganism belonging to genus *Bacillus* may be, for example, *B. subtilis*. The microorganism belonging to genus *Staphylococcus* may be, for example, *S. epidermidis*. In some embodiments, it is confirmed that the aptamer of the present invention specifically binds to 6 microorganisms including *E. coli, E. aerogenes, K. pneumoniae, C. freundii, B. subtilis*, and *S. epidermidis*.

The aptamer may include, for example, nucleotide sequences of SEQ ID NO: 1 to 21, or a combination thereof. For example, the aptamer may include a nucleotide sequence of SEQ ID NO: 19 or 21. In addition, the aptamer may include a nucleotide sequence which has at least 90% homology with any of SEQ ID NO: 1 to 21. For example, at least one nucleotide of any nucleotide sequences of SEQ ID NO: 1 to 21 may undergo a substitution, an insertion, a deletion, an addition, or a combination thereof.

The aptamer may include a detectable label attached thereto. The detectable label may be a moiety which may be detected by detection methods known in the art. For example, the detectable label may be an optical label, an electrochemical label, a radioisotope or a combination thereof. The detectable label may be attached to a specific base of the aptamer, a specific site of a specific structure such as a hairpin-loop structure of the aptamer, or a 3'-terminus or 5'-terminus of the aptamer.

The optical label may be, for example, a fluorescent material. The fluorescent material may be selected from the group consisting of fluorescein, 6-FAM, rhodamine, Texas Red, tetramethylrhodamine, carboxyrhodamine, carboxyrhodamine 6G, carboxyrhodole, carboxyrhodamine 110, Cascade Blue, Cascade Yellow, coumarin, cyanine 2 (Cy2), Cy3, Cy3.5, Cy5, Cy5.5, Cy-chrome, phycoerythrin, peridinin chlorophyll (PerCP)-a protein, PerCP-Cy5.5, 6-carboxy-4',5'-dichloro-2',7'-dimethoxyfluorescein (6-JOE), NED, 5- (and -6)-carboxy-X-rhodamine (ROX), HEX, Lucifer Yellow, Marina Blue, Oregon Green 488, Oregon Green 500, Oregon Green 514, Alexa Fluor, 7-amino-4-methylcoumarin-3-acetic acid, BODIPY FL, BODIPY FL-Br 2, BODIPY 530/550, a conjugated compound thereof, and a combination thereof. For example, the fluorescent material may be fluorescein, Cy3, or Cy5.

In addition, the optical label may be an enzyme, and such an enzyme may be used for enzyme-linked immunosorbent assay (ELISA). Examples of the enzyme include alkaline phosphatase (ALP), horseradish peroxidase, luciferase, and glucose oxidase. When an enzyme is used as the optical label, chemiluminescence materials, such as luminol, isoluminol, luciferin, lucigenin, 3-(2'-Spiroadamantane)-4-methoxy-4-(3"-phosphoryloxy)phenyl-1,2-dioxetane (AMPPD), and Disodium 3-(4-methoxyspiro {1,2-dioxetane-3, 2'-(5'-chloro)tricyclo[3.3.1.13,7]decan}-4-yl) phenyl phosphate (CSPD), may be used to induce a chemiluminescent reaction. In addition, other materials may be appropriately selected by one of ordinary skill in the art.

In addition, the optical label may be a pair of fluorescence resonance energy transfers (FRETs) that include a donor fluorophore and acceptor fluorophore separated from each other by a suitable distance in which the fluorescence emission of the donor is inhibited by the acceptor. The donor fluorophore may include FAM, TAMRA, VIC, JOE, Cy3, Cy5 and Texas Red. The acceptor fluorophore may be selected such that excitation spectrum thereof overlaps emission spectrum of the donor. Also, the acceptor may be a non-fluorescent acceptor that quenches a broad spectrum of donors. Other examples of donor-acceptor FRET pairs are already known in the art.

The electrochemical label may include an electrochemical label known in the art. For example, the electrochemical label may be methylene blue.

According to another aspect of the present invention, provided is a composition for simultaneously detecting two or more microorganisms, the composition including the aptamer.

The aptamer included in the composition is defined as described above. Here, the aptamer may be a nucleic acid aptamer simultaneously and selectively binding to two or more microorganisms. The nucleic acid may be DNA, RNA, PNA, or a combination thereof, and for example, DNA. The aptamer may be a single-stranded nucleic acid aptamer. The aptamer may specifically bind to a surface of each of the two or more microorganisms. The aptamer may commonly and selectively bind to, for example, 6 microorganisms. Such microorganisms may be selected from the group consisting of microorganisms belonging to, for example, genera *Escherichia, Enterobacter, Klebsiella, Citrobacter, Bacillus*, and *Staphylococcus*. For example, when the aptamer targets 2 or more microorganisms, at least one of the target microorganisms may be selected from the above-described group. The aptamer may include, for example, a nucleotide sequence of SEQ ID NO: 19 or 21 or a combination thereof. The aptamer may include a detectable label attached thereto. The detectable label may be, for example, an optical label, an electrochemical label, a radioisotope or a combination thereof.

The composition may further include a material known to be required for a selective binding between the aptamer and target materials. The composition may further include a factor required for promoting the formation of a specific target microorganisms-aptamer complex or for inhibiting the formation of a non-specific microorganisms-aptamer complex, such as salmon sperm DNA, BSA, Tween-20, and/or PEG. In addition, the composition may further include instructions describing a method of identifying the target microorganism.

According to another aspect of the present invention, provided is a biosensor for simultaneously detecting two or more microorganisms, the biosensor including the aptamer.

The aptamer included in the biosensor is defined as described above. Here, the aptamer may be a nucleic acid aptamer simultaneously and selectively binding to two or more microorganisms. The nucleic acid may be DNA, RNA, PNA, or a combination thereof, and for example, DNA. The aptamer may be a single-stranded nucleic acid aptamer. The aptamer may specifically bind to a surface of each of the two or more microorganisms. The aptamer may commonly and selectively bind to, for example, 6 microorganisms. Such microorganisms may be selected from the group consisting of microorganisms belonging to, for example, genera *Escherichia, Enterobacter, Klebsiella, Citrobacter, Bacillus*, and *Staphylococcus*. For example, when the aptamer targets 2 or more microorganisms, at least one of the target microorganisms may be selected from the above-described group. The aptamer may include, for example, nucleotide sequences of SEQ ID NO: 1 to 21 or a combination thereof. The aptamer may include a detectable label attached thereto. The detectable label may be an optical label, an electrochemical label, a radioisotope or a combination thereof. The biosensor including the optical label may be, for example, a sensor which utilizes an FRET effect or an enzyme reaction. The biosensor including the electrochemical label may be, for example, based on the principle that an electrochemical signal changes as the label move away from an electrode or move toward an electrode or separate from the aptamer due to a structural change in the aptamer. The biosensor may further include a factor for detecting target microorganisms, such as an enzyme, an antibody, or a nucleic acid.

The biosensor may be one which includes a substrate where two or more of the aptamers are immobilized, and for example, may be in the form of an array. The array as used herein refers to a state where a plurality of specific molecules are immobilized and fixed to a certain region on the substrate. The array may include the substrate and an immobilized region formed on the substrate which includes the aptamer capable of binding to target materials. The aptamer may be covalently attached to the substrate within the immobilization region. The aptamer may further include a plurality of compounds with functional groups that may be covalently attached to the substrate. The functional groups may be any material as long as it is capable of attaching the aptamer, and for example, may be an aldehyde, an epoxy, or an amine group. Each of the compounds may be a siloxane having an aldehyde, an epoxy, or an amine group at the end. The material for the substrate may be, for example, glass, silicone, polypropylene, and polyethylene.

According to another aspect of the present invention, provided is a kit for simultaneously detecting two or more microorganisms, the kit including the aptamer.

The aptamer included in the kit is defined as described above. Here, the aptamer may be a nucleic acid aptamer simultaneously and selectively binding to two or more microorganisms. The nucleic acid may be DNA, RNA, PNA, or a combination thereof, and for example, DNA. The aptamer may be a single-stranded nucleic acid aptamer. The aptamer may specifically bind to a surface of each of the two or more microorganisms. The aptamer may commonly and selectively bind to, for example, 6 microorganisms. Such microorganisms may be selected from the group consisting of microorganisms belonging to, for example, genera

*Escherichia, Enterobacter, Klebsiella, Citrobacter, Bacillus*, and *Staphylococcus*. For example, when the aptamer targets 2 or more microorganisms, at least one of the target microorganisms may be selected from the above-described group. The aptamer may include, for example, a nucleotide sequence of SEQ ID NO: 1 to 21 or a combination thereof. The aptamer may include a detectable label attached thereto. The detectable label may be, for example, an optical label, an electrochemical label, a radioisotope or a combination thereof.

The kit may be in the form of a chip where the aptamer is immobilized on the chip, or in the form of an array where the aptamer is immobilized on the substrate. The immobilization of DNA aptamers on a chip or a substrate may be performed by using a method known in the art. For example, a chip or a substrate may be modified with streptavidin, an end of an aptamer is biotinylated, and then, the biotin of the aptamer and the streptavidin of a support are bonded together to be immobilized. The array may include the substrate and an immobilized region formed on the substrate which includes the aptamer capable of binding to two or more target microorganisms. The aptamer may be covalently attached to the substrate within the immobilization region. The aptamer may further include a plurality of compounds with functional groups that may be covalently attached to the substrate. The functional groups may be any material as long as it is capable of attaching the aptamer, and for example, may be an aldehyde, an epoxy, or an amine group. Each of the compounds may be a siloxane having an aldehyde, an epoxy, or an amine group at the end. The material for the substrate may be, for example, glass, silicone, polypropylene, and polyethylene.

According to another aspect of the present invention, provided is a method of manufacturing a nucleic acid aptamer capable of commonly and selectively binding to two or more microorganisms: the method including a) mixing at least one target material with nucleic acid pools consisting of random nucleic acid sequences or nucleic acids having nucleic acid sequences that are capable of binding to a target microorganism so as to induce a binding therebetween; b) removing nucleic acids that are not bound to the target microorganism; c) separating nucleic acids that are bound to the target microorganism from the target microorganism; d) amplifying the nucleic acids obtained in step c) via PCR; and e) sequentially repeating the steps a) to d) with respect to the amplified nucleic acids and each remaining target microorganism.

The method of manufacturing the aptamer is as follows. First, the method includes a) mixing at least one target material with nucleic acid pools consisting of random nucleic acid sequences or nucleic acids having nucleic acid sequences that are capable of binding to a target microorganism so as to induce a binding therebetween. Here, the nucleic acids included in the nucleic acid pools may be referred to as candidates for the aptamer to be manufactured. For example, the nucleic acid pools may include sequences of nucleic acids capable of specifically binding to target microorganisms. These nucleic acids may include, for example, a sequence capable of selectively binding to the target microorganisms in the center, and a primer region for PCR at both ends. The number of bases of the nucleic acids in the center that are capable of selectively binding to the target microorganisms may be, for example, in a range of 10 to 60, 20 to 50, 30 to 55, or 35 to 50. In some embodiments, the target microorganisms may be mixed with DNA pools having a primer region for PCR at both ends and any 40 bases in the center.

The nucleic acid may be DNA, RNA, PNA, or a combination thereof, and for example, DNA. In regard to the method of manufacturing the aptamer of the present invention, the aptamer may commonly and selectively bind to, for example, 2 or more, 3 or more, 4 or more, 5 or more, 6 or more, 7 or more, 8 or more, 9 or more, or 10 or more microorganisms. In addition, the aptamer of the present invention may commonly and selectively bind to, for example, 2 to 20, 3 to 18, 4 to 16, 5 to 14, 6 to 12, 6 to 10, 6 to 9, or 6 to 8 microorganisms. In addition, the aptamer of the present invention may commonly and selectively bind to, for example, 2, 3, 4, 5, or 6 microorganisms.

The microorganisms to which the aptamer commonly and selectively bind may be selected from the group consisting of microorganisms belonging to genera *Escherichia, Enterobacter, Klebsiella, Citrobacter, Bacillus*, and *Staphylococcus*. For example, at least one of the target microorganisms may be selected from the above-described group. In addition, the target microorganisms may be genera *Escherichia, Enterobacter, Klebsiella, Citrobacter, Bacillus*, and *Staphylococcus*. The microorganism belonging to genus *Escherichia* may be, for example, *E. coli*. The microorganism belonging to genus *Enterobacter* may be, for example, *E. aerogenes*. The microorganism belonging to genus *Klebsiella* may be, for example, *K. pneumoniae*. The microorganism belonging to genus *Citrobacter* may be, for example, *C. freundii*. The microorganism belonging to genus *Bacillus* may be, for example, *B. subtilis*. The microorganism belonging to genus *Staphylococcus* may be, for example, *S. epidermidis*. In some embodiments, an aptamer that is capable of specifically binding to 6 microorganisms including *E. coli, E. aerogenes, K. pneumoniae, C. freundii, B. subtilis*, and *S. epidermidis* is manufactured.

Next, the method includes b) removing nucleic acids that are not bound to the target microorganisms. The step b) refers to separation or removal of the nucleic acids that are not bound to the target microorganisms from the target microorganisms and the nucleic acids that are bound thereto. The separation of the nucleic acids that are not bound to the target microorganisms may be performed by, for example, centrifugation.

Next, the method includes c) separating nucleic acids that are bound to the target microorganisms from the target microorganisms. After the nucleic acids that are not bound to the target microorganisms are removed in step b), nucleic acids that are bound to the microorganisms may be separated therefrom. For example, a sample including the nucleic acids that are bound to the target microorganisms is heated at a temperature in a range of about 85° C. to about 99° C. for 3 to 15 minutes, thereby separating the nucleic acids from the target microorganisms.

Next, the method includes d) amplifying the nucleic acids obtained in step c) via PCR. PCR may be performed by using primer pairs that are complementary to the primer region for PCR at both ends in the nucleic acids. The primer as used herein may include a fluorescent label attached to at least one of the primer pairs. In some embodiments, PCR is performed by using primers with fluorescein attached thereto. Afterwards, the method may further include identifying sizes of the nucleic acids via electrophoresis.

In some embodiments, at least one of the primer pairs may be attached with biotin. After PCR is performed by using the biotin-attached primer, single-stranded nucleic acids may be separated from the amplified nucleic acids with a double helix structure by using magnetic beads coated with biotin proteins on the surface.

Next, the method includes e) repeating steps a) to d) by using the amplified nucleic acids in step d) with respect to other target microorganisms. For example, steps a) to d) are performed in the same manner by using the amplified nucleic acids in step d) and any one of target microorganisms other than the target microorganism undergone the steps above. Afterwards, steps a) to d) are performed again in the same manner by using the amplified nucleic acids and other target microorganisms. Finally, steps a) to d) are sequentially performed with respect to each of all the target microorganisms.

The method of manufacturing the aptamer may further include repeating steps a) to e) 1 to 5 times, 2 to 4 times, or 2 to 3 times. Here, the aptamers manufactured or selected according to the repeating of steps a) to e) may have high selectivity for target microorganisms.

The method of manufacturing the aptamer may further include selecting nucleic acids that are capable of more specifically and strongly binding to target microorganisms as a result of analyzing secondary structures of the nucleic acids.

Hereinafter, the present invention is described in greater detail with reference to embodiments. However, the embodiments are for illustrative purposes only and do not limit the scope of the present invention.

EXAMPLE 1

Preparation of a DNA Aptamer Having High Selectivity in a Simultaneous and Common Way for 6 Kinds of Microorganisms 1-1. Preparation of Target Microorganisms and DNA Pools Each kind of microorganisms (i.e., *E. coli, E. aerogenes, K. pneumoniae, C. freundii, B. subtilis,* and *S. epidermidis*) was cultured in a 100 mL nutrient broth (NB) until the concentration of each kind of microorganism reached $10^8$ CFU/mL. Then, 1 mL of the culture medium was subjected to centrifugation to separate the microorganism. The separated microorganism was washed off 3 times with a PBS buffer (at pH 7.0) and suspended in a binding buffer (1×PBS, 0.1 mg/ml salmon sperm DNA, 1% BSA, and 0.05% tween-20).

In order to manufacture an aptamer, DNA pools with a length of 76-mer were synthesized, wherein the DNA pools consist of fixed sequence regions for PCR at both ends and 40 random base sequences in the center. Here, the DNA pools were synthesized to have sequences (SEQ ID NO: 22) below. The synthesis of DNA pools was requested at Genotech Inc.(Korea) to be carried out in a chemical way. As shown in the sequences below, the DNA pools consist of fixed sequence regions to which primer pairs are annealed at both ends, and a randomly arranged base sequence region (n) in the center. Here, n generally refers to a constitution consisting of 40 random bases of A, G, T and C. However, the total number of bases is not limited to 40, and a few bases may be added or omitted via repeated PCR and cloning of SELEX process.

```
                                    (SEQ ID NO: 22)
5'-CGTACGGAATTCGCTAGC-n-GGATCCGAGCTCCACGTG-3'
```

Finally, a random ssDNA pools having $10^{15}$ mutually different base sequences was synthesized.

1-2. Screen of Aptamers

The synthesized ssDNA pools having $10^{15}$ mutually different base sequences were mixed with *E. coli* suspension ($10^7$ cells) as a first target material at room temperature for an hour. Then, an ssDNA that was not bound to *E. coli* was removed by centrifugation. Next, in order to remove an ssDNA having weak binding strength among ssDNAs bound to *E. coli*, the mixture was washed off 3 times with a buffer solution. After an ssDNA that was bound to *E. coli* was re-suspended in sterile distilled water, in order to separate the bound ssDNA from *E. coli*, the resultant mixture was heated at a temperature of 95° C. for 10 minutes, and the ssDNA separated from *E. coli* was collected by centrifugation. The collected ssDNA, i.e., the ssDNA specifically binding to *E. coli*, was amplified via PCR to increase amounts thereof. At least one (e.g., primer for PCR) of primer pairs below used for PCR was labeled with a fluorescent material and the other one (e.g., primer for PCR) of the two primers was labeled with biotin to separate dsDNAs of the PCR products into ssDNAs.

```
Primer for PCR:
                                    (SEQ ID NO: 23)
5'-fluorescein-CGTACGGAATTCGCTAGC-3'

Primer for PCR:
                                    (SEQ ID NO: 24)
5'-biotin-CACGTGGAGCTCGGATCC-3'
```

PCR was performed under the conditions of 95° C. (30 seconds), 56.3° C. (30 seconds) and 72° C. (10 seconds), by mixing 5 μl of ssDNA (which is approximately 100 ng), 2.5 μL of each prime, 25 μl of PCR master mix, and 15 μl of distilled water, and the number of repeating cycle was 8. Electrophoresis was performed in a 2% agarose gel to identify the proper performance of PCR (100 V, 30 min), and then, the PCR products were purified by using a PCR purification kit (MinElute PCR purification Kit, Qiagen). Afterwards, a dsDNA with a double helix structure of the PCR product was denatured into a ssDNA by using magnetic beads coated with avidin (streptavidin) on the surface. Then, the ssDNA was washed off twice with a PBS buffer by using 50 μl of the magnetic beads coated with avidin on the surface, and the resultant was mixed with 50 μl of the PCR products at room temperature for 30 minutes. Then, the resultant was washed off with a PBS buffer by using a magnet. Here, 500 μl of 0.2 M NaOH was added thereto, and the mixture was allowed to react for 10 minutes at room temperature in order to collect ssDNA by using a magnet. The collected ssDNA was concentrated/purified for the next round's screen procedure.

For the next round's ssDNA selecting procedure, an ssDNA specifically binding to *E. coli* was mixed with a second target microorganism, *E. aerogenes*, for 1 hour. Afterwards, an ssDNA that was not bound to *E. aerogenes* was removed and an ssDNA that was bound to *E. aerogenes* was collected. Then, the collected ssDNA was subjected to a series of steps in the same manner as in the steps using *E. coli*, the steps including PCR amplification, purification of the PCR products, denaturation of dsDNA into ssDNA, and concentration/purification of the ssDNA. For the next round's ssDNA screening procedure, target materials including *K. pneumonia* as the third target material, *C. freundii* as the fourth target material, *B. subtilis* as the fifth target material, and *S. epidermidis* as the sixth target material were used, and an ssDNA that was not bound to the target materials removed and an ssDNA that was bound to the target materials was collected. Then, the collected ssDNA was subjected to a series of steps in the same manner as in the steps using E. coli, the steps including PCR amplification, purification of the PCR products, denaturation of dsDNA into ssDNA, and concentration/purification of the ssDNA. Afterwards, a total of 3 selection procedures were repeated with respect to 6 kinds of microorganisms, thereby finally obtaining a universal ssDNA that is commonly and selectively binding to 6 kinds of microorganisms.

1-3. Analysis of the Obtained ssDNA Base Sequences

The finally obtained ssDNA pool was cloned by using a cloning kit (TOPO cloning kit, Invitrogen), and plasmids were extracted from each colony so as to analyze nucleotide sequences of the ssDNA. As a result, a total of 65 different nucleotide sequences were obtained, and except overlapping sequences, a total of 21 different nucleotides sequences of the ssDNA were finally obtained. Table 1 below shows the results of analyzing 21 different nucleotide sequences of the ssDNA commonly and selectively binding to 6 kinds of microorganisms.

TABLE 1

| Name | Sequence of random region | SEQ ID NO |
|---|---|---|
| No. 1 | 5'-GGGCGGGGGTGCTGGGGGAATGGAGTGCTGCGTGCTGCGG-3' | 1 |
| No. 2 | 5'-CATATCCGCGTCGCTGCGCTCAGACCCACCACTACGCACC-3' | 2 |
| No. 3 | 5'-CATATCCGCGTCGCTGCGCTCAGACCCACCACCCGCCC-3' | 3 |
| No. 4 | 5'-CGAACGTTGCGGTGTGGAACTTCGCGAGCA-3' | 4 |
| No. 5 | 5'-TGCGGACTCGCGATGCTACTTCTGATGATA-3' | 5 |
| No. 6 | 5'-CATATCCGCGTCGCTGCGCTCAGACCCACCACCACGCACC-3' | 6 |
| No. 7 | 5'-CGACCGCAGGTGCACCGGGCGACGTCTCTGGGTGTGGTGA-3' | 7 |
| No. 8 | 5'-TGCGGACTCATGATGCTACTTCTGATGATA-3' | 8 |
| No. 9 | 5'-GGGCGGGGGTGCTGGGGGAATGGAGTGCTGCGTGCTGCG-3' | 9 |
| No. 10 | 5'-GGCGGGGGTGCTGGGAGAATGGAGTGCTGCGTGCTGCAG-3' | 10 |
| No. 11 | 5'-ATATCCGCGTCGCTGCGCTCAGACCCACCACCACGCACC-3' | 11 |
| No. 12 | 5'-CATATCCGTGTCGCTGCGCTCAGACCCACCACCACGCACC-3' | 12 |
| No. 13 | 5'-GGACTGGAGTCTAGACCGGGTAGCTGTGGT-3' | 13 |

TABLE 1-continued

| Name | Sequence of random region | SEQ ID NO |
|---|---|---|
| No. 14 | 5'-CGACGCGCGTTGGTGGTGGATGGTGTGTTACACGTGTTGT-3' | 14 |
| No. 15 | 5'-CGGGGTGGGACCAGTCTTGCGCGGGTGAC-3' | 15 |
| No. 16 | 5'-CGACCGCAGGTGCACTGGGCGACGTCTCTGGGTGTGGTGT-3' | 16 |
| No. 17 | 5'-CGAACGGTGCGGTGTGGAACTTCGCGAGCA-3' | 17 |
| No. 18 | 5'-GGGCAGGTGTGCTGGGGGAATGGAGTGCTGCGTGCTGCGG-3' | 18 |
| No. 19 | 5'-GGACCGCAGGTGCACTGGGCGACGTCTCTGGGTGTGGTGT-3' | 19 |
| No. 20 | 5'-CGAACGTTGCGGTGTGGACCTTCGCGAGCA-3' | 20 |
| No. 21 | 5'-CGACCGCAGGTGCACTGGNCGACGTCTCTGGGTGTGGTGT-3' | 21 |

EXAMPLE 2

Analysis of DNA Aptamers in Terms of a Secondary Structure of the Selected ssDNA, Binding Capability and Selectivity of the Aptamer with Respect to 6 Kinds of Microorganisms 2-1. Analysis of Secondary Structure of the Selected ssDNA A secondary structure of the selected ssDNA having 21 different nucleotide sequences was analyzed by using an Mfold program that is available for free on the web Zuker, M. Nucleic Acids Res. 2003, 31, 3406). Based on the resulting secondary structures of the ssDNA having 21 different nucleotide sequences, two kinds of the nucleotide sequences (i.e., No. 6 and No. 19) of the DNA aptamer that were expected to have the highest affinity for all of the 6 kinds of microorganisms were selected so as to analyze selectivity and affinity for 6 kinds of microorganisms.

2-2. Affinity and Selectivity Analysis of DNA Aptamers on 6 Kinds of Microorganisms Each kind of microorganisms (i.e., E. coli, E. aerogenes, K. pneumoniae, C. freundii, B. subtilis, and S. epidermidis) was cultured in a 100 mL NB until the concentration of each kind of the microorganisms reached $10^8$ CFU/mL. Then, 1 mL of the culture medium was subjected to centrifugation to separate the microorganism. The 6 kinds of the microorganisms that were each separated were washed off 3 times with a PBS buffer (at pH 7.0) and suspended in a binding buffer (1×PBS, 0.1 mg/mL salmon sperm DNA, 1% BSA, and 0.05% tween-20). 100 uL ($10^7$ cells) of each of the 6 kinds of the microorganisms was mixed with 100 uL of fluorescence-labeled ssDNA at various concentrations (e.g., 0, 10, 25, 50, 100, 250, and 500 nM) and allowed to react at room temperature for 1 hour. Upon reaction, the resultants were washed off 3 times with a PBS buffer to remove ssDNAs that were not bound to the surface of the microorganism, and the fluorescence intensity of the ssDNAs that were bound to the microorganism was measured. The fluorescence intensity at each of the various ssDNA concentrations was plotted to obtain a dissociation constant in a graph via a non-linear regression method and single-region saturation ligand binding method by using a SigmaPlot program based on the equation, $F=B_{max}*C/(K_d+C)$ (wherein F indicates the fluorescence intensity, $B_{max}$ indicates the location of maximum binding, $K_d$ indicates a dissociated constant, and C indicates concentration of ssDNA).

As a result, it was confirmed that both nucleotide sequences (i.e., No. 6 and No. 19) of the ssDNA had significantly high affinity commonly for 6 kinds of the microorganisms, and the results thereof are shown in Table 3 below. The dissociation constants of the two kinds of nucleotide sequences with high affinity for all of the 6 kinds of microorganisms were each shown in Table 2 below.

TABLE 2

| Types of microorganisms | No. 06 $K_d$ | No. 19 $K_d$ |
|---|---|---|
| E. coli | 27.17 | 38.46 |
| E. aerogenes | 46.38 | 33.66 |
| K. pneumoniae | 9.22 | 16.26 |
| C. freundii | 16 | 25.64 |
| B. subtilis | 9.97 | 18.8 |
| S. epidermidis | 16.38 | 13.72 |

Figure 9:
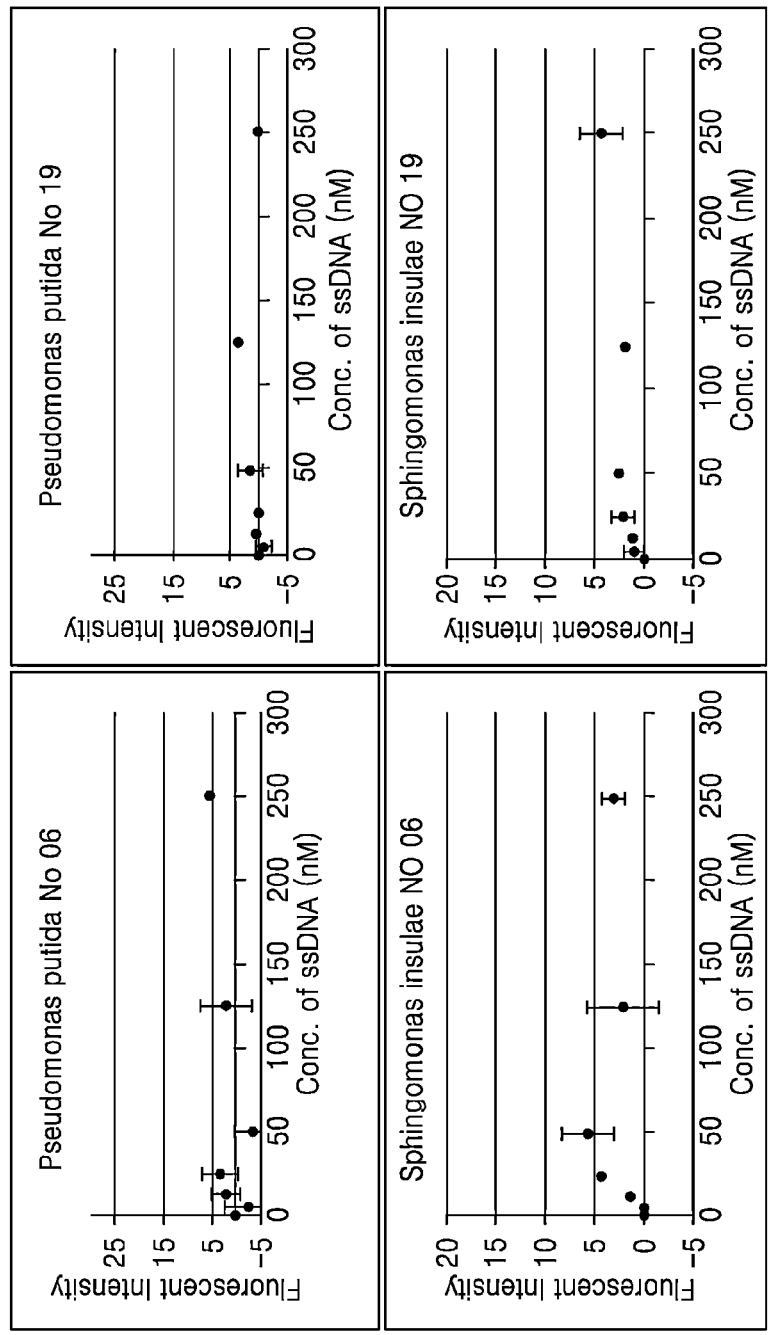
FIG. 9 shows the results of analyzing specificity of DNA aptamer No. 06 and DNA aptamer No. 19 based on fluorescence intensity of aptamers each binding to *Pseudomonas putida* and *Sphingomonas insulae*.

In order to confirm the selectivity of the two types of the ssDNAs on 6 kinds of the microorganisms, selectivity analysis of the two types of the ssDNAs on other two kinds of microorganisms, i.e., *Pseudomonas putida* and *Sphingomonas insulae* that were not involved in the ssDNA aptamer selecting procedure, was performed. 100 uL (10' cells) of each of the other two kinds of the microorganisms was allowed to react with 100 uL of fluorescence-labeled ssDNA at various concentrations (e.g., 0, 10, 25, 50, 100, 250, and 500 nM) at room temperature for 1 hour. Upon reaction, the resultants were washed off with a PBS buffer to remove ssDNAs that were not bound to the surface of the microorganism, and the fluorescence intensity of the ssDNAs that were bound to the microorganism was measured and compared. As shown in FIG. 9 below, the fluorescence intensity of the ssDNAs (No. 06 and No. 19) on the two kinds of the microorganisms including *P. putida* and *S. insulae* was very low.

One aspect of the present invention provides an aptamer that is applicable to simultaneously detect two or more kinds of microorganisms that are mainly present in a limited environment. Accordingly, it is possible to develop a universal receptor that is capable of generally diagnosing targets in populations, and a diagnostic system using the universal receptor. Another aspect of the present invention provides a method of manufacturing the aptamer so as to provide a probe that is capable of detecting or diagnosing various types of microorganisms at the same time. In addition, a method of finding an aptamer having such features may be provided.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A nucleic acid aptamer commonly and specifically binding to microorganisms from two or more genera of microorganisms selected from the group consisting of *Escherichia, Enterobacter, Klebsiella, Citrobacter, Bacillus,* and *Staphylococcus*, wherein the nucleic acid aptamer comprises the nucleotide sequence of any one of SEQ ID NO: 2 to 13, 15, 17, 18, 20 and 21.

2. The nucleic acid aptamer of claim 1, wherein the nucleic acid aptamer comprises a detectable label attached thereto.

3. A composition for simultaneously detecting two or more microorganisms comprising the nucleic acid aptamer of claim 1.

4. A biosensor for simultaneously detecting two or more microorganisms comprising the nucleic acid aptamer of claim 1.

5. The nucleic acid aptamer of claim 1, wherein the nucleic acid aptamer is immobilized to a substrate.

6. The composition of claim 3, wherein the nucleic acid aptamer is immobilized to a substrate.

7. The composition of claim 6, wherein two or more nucleic acid aptamers are immobilized to a substrate in the form of an array.

8. The biosensor of claim 4, wherein the nucleic acid aptamer is immobilized to a substrate.

9. The biosensor of claim 8, wherein two or more nucleic acid aptamers are immobilized to a substrate in the form of an array.

* * * * *